(12) United States Patent
Higgins et al.

(10) Patent No.: US 12,714,826 B2
(45) Date of Patent: Aug. 25, 2026

(54) ECHOLUCENT INTRAVASCULAR CANNULA AND ECHOLUCENT LOCATING OF PORTIONS OF INTRAVASCULAR MEDICAL DEVICES

(71) Applicant: Cardiovascular Systems, Inc., St. Paul, MN (US)

(72) Inventors: Joseph P. Higgins, Minnetonka, MN (US); Grant A. Adams, New Brighton, MN (US); Ric A. Gould, Brooklyn Park, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 1136 days.

(21) Appl. No.: 17/663,772

(22) Filed: May 17, 2022

(65) Prior Publication Data

US 2022/0387755 A1 Dec. 8, 2022

Related U.S. Application Data

(60) Provisional application No. 63/196,307, filed on Jun. 3, 2021.

(51) Int. Cl.
*A61M 25/01* (2006.01)

(52) U.S. Cl.
CPC ................................ *A61M 25/0108* (2013.01)

(58) Field of Classification Search
CPC ........ A61M 25/0108; A61M 2025/006; A61B 1/0055
See application file for complete search history.

(56) References Cited

U.S. PATENT DOCUMENTS

2008/0154136 A1 6/2008 Webler
2010/0160731 A1 6/2010 Giovannini et al.
2015/0238730 A1 8/2015 Corman et al.
2017/0021127 A1* 1/2017 Manouchehr ....... A61M 5/3291
2020/0315639 A1* 10/2020 Nicholson .............. A61F 2/958

FOREIGN PATENT DOCUMENTS

WO 2017/161166 A1 9/2017

OTHER PUBLICATIONS

International Search Report and Written Opinion issued in PCT/US2022/72440, dated Oct. 5, 2022.

* cited by examiner

*Primary Examiner* — Bradley J Osinski
(74) *Attorney, Agent, or Firm* — Kagan Binder, PLLC

(57) ABSTRACT

A medical tube or cannula comprising enhanced imaging structure and/or materials is provided. In some embodiments, an otherwise solid echogenic band may be interrupted by echolucent features and/or materials. In other embodiments, an echogenic band may be adjacent to an echolucent band, while in other embodiments one or more echolucent bands may be provided. In some cases, two or more spaced-apart echolucent bands may be provided. In some embodiments, an echolucent band may comprise an echogenic feature or materials. Generally, the juxtaposition of echogenic and echolucent materials enhances the imaging contrast of an intravascular device and allows easy identification and positioning of the juxtaposed echogenic and echolucent regions.

3 Claims, 11 Drawing Sheets

ECHOLUCENT INTRAVASCULAR CANNULA AND ECHOLUCENT LOCATING OF PORTIONS OF INTRAVASCULAR MEDICAL DEVICES

CROSS-REFERENCE TO RELATED APPLICATIONS

This application claims priority to Provisional Application No. 63/196,307, filed Jun. 3, 2021 and entitled ECHOLUCENT LOCATING OF PORTIONS OF INTRAVASCULAR MEDICAL DEVICES, the entirety of which is incorporated herein by reference.

STATEMENT REGARDING FEDERALLY SPONSORED RESEARCH OR DEVELOPMENT

Not Applicable

FIELD OF THE INVENTION

Generally, medical devices such as catheters for intravascular procedures such as angioplasty, lithoplasty, atherectomy or ablation, thrombectomy and/or cannulas for blood pumps wherein the catheters or cannulas define at least one echolucent opening or region enabling non-invasive imaging location of the cannula is positioned within a patient's body.

BACKGROUND OF THE INVENTION

Description of the Related Art

The related art comprises catheters, and other related medical devices, generally used in intravascular procedures such as, without limitation, angioplasty, lithoplasty, atherectomy, stenting and/or ablation. Such catheters are well known to the artisan and may comprise and/or facilitate delivery of working elements such as a balloon or an abrasive element or stenting element. It will be desirable to image the location of the working element in relation to aspects, generally distal aspects, of the catheter.

Further, in hemodynamic devices such as blood pumps, e.g., ventricular assist pump devices, components of the device should be positioned relative to particular anatomical features during use. For example, portions of a cannula adjacent inlet and outlet windows of a blood pump desirably may be positioned relative to an outflow tract and the aortic valve within a patient's heart during use.

We describe herein exemplary blood pumps to assist in illustrating the various inventive concepts, but the basic problems in imaging and proposed solutions discussed herein apply with equal force to intravascular catheters and other related medical devices, which will readily be recognized by the skilled artisan.

With reference to FIG. 1, the human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a flow inducer, known in the art as component that directs flow into the impeller from the inflow apertures or inlet; a rotational impeller; and a flow diffuser and/or outflow structure known in the art as functioning to straighten or redirecting the rotational flow created by the rotational impeller into axial flow; and an outflow aperture(s). An exemplary VAD device is illustrated in FIG. 2, where a known LVAD blood pump 1 is illustrated. LVAD blood pump 100 comprises a cannula 14 with inflow apertures 12 on the left side (inflow end) of the illustration and outflow apertures 10 on the right side (outflow end) of the image. The motor is shown as rotationally connected with a rotational drive shaft that is, in turn, connected with the impeller or rotor or pump assembly. Motor is illustrated as located outside of the patient's body. However, as is well known in the art, the motor may be implanted and housed within a housing or cannula, wherein the motor is typically mounted on the proximal side of the rotor or impeller or pump assembly and in operational rotational connection therewith. Either of these configurations may be used together with various embodiments of the present invention as described herein.

The entire length of outer housing (or cannula) 14 is shown in FIG. 2 as comprising a relatively constant diameter from the inlet or inflow apertures 12 to the outlet or outflow apertures 10. Portions of the cannula 14 may be expandable. Guide wire 6 may be positioned alongside the exterior of the device, as shown, until reaching the inlet apertures 12 where it enters the lumen of cannula 14 and extends distally therefrom as shown. Alternatively, guide wire 16 may be guided through at least a portion of the housing or cannula 14. The cannula 14 may be formed of a stent or a mesh or a laser-cut tube or a polymer, or equivalents thereof and may in sonic embodiments comprise a braid and/or be covered by a fluid impermeable coating and/or membrane and/or jacket. The portion of the cannula 14 disposed between inlet 12 and outlet 10, marked as element 102, may comprise a proximal section 105, central section 104 and distal section 108, wherein the cannula 14 is effectively fluid impermeable. The pump assembly as illustrated includes an impeller within cannula 14 (not shown but as is well known to the artisan and located distal to the outlet 10) and a connection region 18 to which is attached the drive shaft as shown.

In order to properly position and locate components of the intravenous medical device including, without limitation, the exemplary blood pump (or intravenous medical device or catheter), a physician may observe the device via non-invasive means (e.g. ultrasound, echocardiogram, x-ray, fluoroscopy) as the device is positioned within a patient's body. Generally, in such devices, a cannula 14 of the exemplary blood pump 1 may include one or more hands or markers that are observable by such means as they produce a stronger reflective signal than the rest of the device, i.e., the bands or markers are echogenic or reflective of, e.g., ultrasonic energy. However, such bands or markers, taken individually, typically do not enable differential location of a particular feature of the device. Moreover, such bands or markers typically comprise material, such as tungsten, that is added to the cannula during manufacturing, thereby increasing complexity and expense of the cannula. Further, such metal bands or markers are highly reflective to ultrasound energy due to the characteristic acoustic impedance of the metallic band or marker. As a result, various and undesirable artifacts may be observed which may, in turn, mask certain significant features of the image. For example in the exemplary blood pump 1, it may be desirable to locate via imaging at least one of the blood pump inlet 12, the blood pump outlet 10 and the blood pump impeller/pump assembly region, and to observe via imaging, and without obstructive reflectance, the positioning and/or functioning of at least these blood pump regions.

It would be advantageous to facilitate and improve imaging of some or all of the described parts or components of the exemplary blood pump during intravascular positioning and while in use. Similarly, exemplary intravascular catheters and related device may benefit from imaging of selected locations and/or regions during use, including but not limited to atherectomy, thrombectomy, angioplasty, lithoplasty, or ablation devices, each such design is well known to the skilled artisan.

The inventions disclosed herein address these, inter alia, issues. The skilled artisan will readily recognize that the issues addressed, and solutions provided, herein apply to intravascular cannulas configured to provide intravascular access for intravascular medical devices in general, including but not limited to catheters and related intravascular working elements or devices, including but certainly not limited to the following which are well known in the art: atherectomy working or abrasive elements, thrombectomy elements, inflatable balloons which may, in the case of lithoplasty, comprise pressure wave generating elements therein, and ablation elements.

The Figures and the detailed description which follow more particularly exemplify these and other embodiments of the invention.

DETAILED DESCRIPTION OF THE INVENTION

Figure 1:
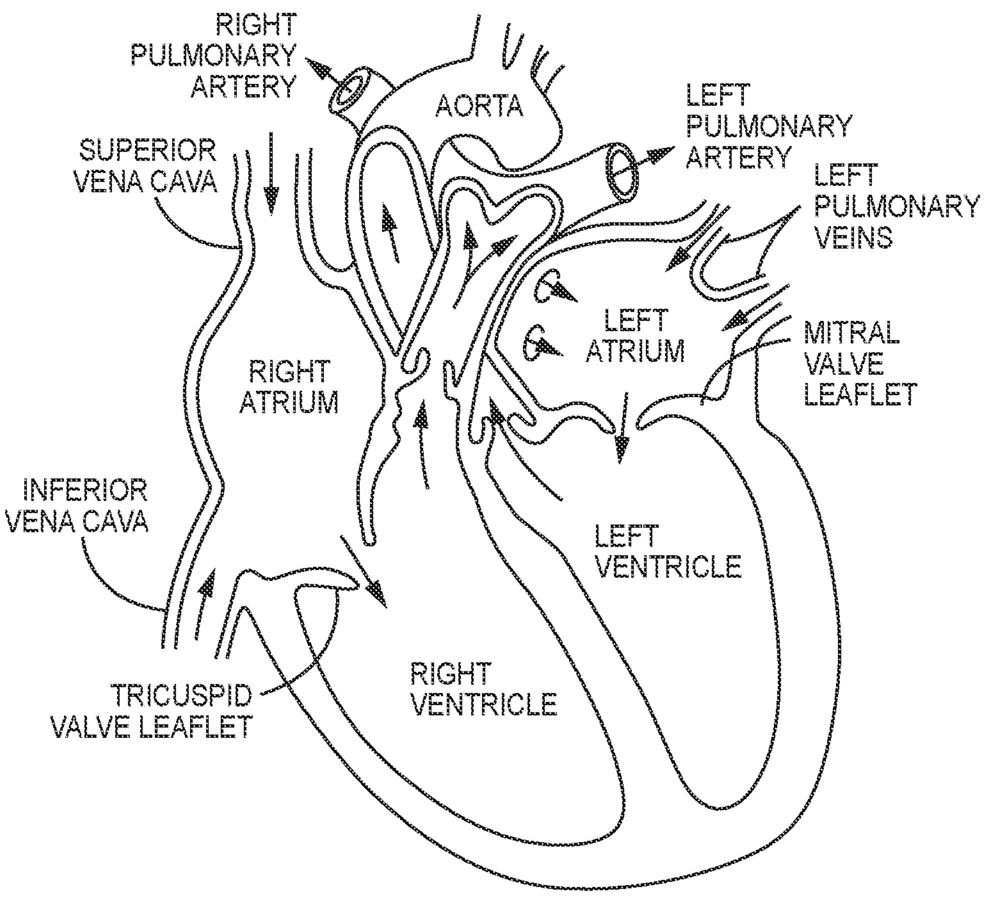
FIG. 1 is a cutaway view of the human heart.

With general reference to the Figures, exemplary cannulas for intravascular medical device such as blood pumps as described above, or other medical devices including but not limited to atherectomy, thrombectomy, lithoplasty, angioplasty and/or ablation are disclosed. As will be further described infra, an outer wall of the exemplary cannula may define at least one opening or aperture therethrough. The at least one opening or aperture is identifiable via non-invasive means (e.g. imaging by ultrasound, echocardiogram, x-ray, and/or fluoroscopy) when the cannula is positioned within a patient's body. For example, the at least one opening or aperture may be less echogenic (i.e. less reflective and more echolucent) than the surrounding or juxtaposed material of the outer wall of the cannula, thereby enabling the at least one opening to be distinguished from the rest of the cannula when observed via the non-invasive means. The edges of the at least one opening or aperture will be more echogenic than the opening or aperture defined by the edges as a result of the imaged contrast between the defined opening or aperture and the edge(s) defining the very echolucent opening or aperture. And, if the at least one opening or aperture is disposed in, or along, or within a region, e.g., a structure or band, that is otherwise relatively echogenic, the edges defining the echolucent opening or aperture will appear very echogenic (very bright in imaging) in comparison with the echolucent opening or aperture, thus allowing the operator to quickly identify the region or band comprising the echolucent opening or aperture and its location thereof. Subsequently, identification of a specific structure of the cannula and/or related medical device, and/or functionality, may be achieved and located, relative to the known position of the at least one (now identified) opening or aperture within the patient's vasculature.

The location or position of the at least one opening or aperture may correspond to a particular feature or element of the device, thereby enabling identification of that feature or element, and/or location of same, relative to an anatomical feature when the cannula is positioned within the patient's body.

In some embodiments, at least one opening or aperture may be located at and/or near the exemplary blood pump impeller region and/or blood inlet region located distal to the impeller region, and/or blood outlet region located proximal to the impeller region. In other embodiments, the cannula may define a plurality of openings which may correspond to a plurality of different features or elements of the device, thereby enabling identification of the plurality of features or elements of the device when the cannula is positioned, or being positioned, within the patient's body. In some such embodiments, the plurality of openings or apertures, and defining edges thereof, may be shaped as one or more of a plurality of different shapes. Additionally, or alternatively, a portion of the cannula that does not define an opening or aperture may correspond to a particular feature of the device.

Alternatively or in addition, the exemplary cannula may comprise a marker band or marker region that is more echogenic (more reflective and less echolucent), or less echogenic (less reflective and more echolucent) than adjacent cannula material, wherein the marker band or marker region is identifiable during the previously described non-invasive imaging means such as ultrasound. In this way, characteristic echolucent areas corresponding with an echogenic marker band or marker region enable imaging location of the echogenic band or region. The at least one echolucent opening or aperture with relatively echogenic edges may be arranged adjacent to or at least partially defined within the echogenic marker band or marker region.

A further alternative may comprise the marker band or marker region formed of primarily (or all) echolucent material. In related embodiments, at least a portion of the echolucent band or region may comprise echogenic material coated thereon and/or embedded or deposited discretely on or within a surface of the echolucent band or region. These embodiments may further comprise at least one opening or aperture with relatively echogenic edges to provide a bright imaging contrast.

Still further, any of the above imaging solutions may be combined. For example, echolucent openings or apertures with relatively echogenic edges may be provided in combination with a marker band or marker region that is at least partially echogenic. The echolucent openings or apertures may be defined through an at least partially echogenic marker band or marker region and/or provided along the cannula adjacent the at least partially echogenic marker band or marker region.

As described further herein, the subject marker echolucent opening(s) or aperture(s) with relatively echogenic edges and/or relatively echolucent band(s) or region(s) may be positioned along the exemplary blood pump cannula to help locate the position of the blood pump inlet, the blood pump outlet and/or the blood pump impeller region or other region of interest. The opening(s) and/or aperture(s) may be relatively echolucent compared with surrounding or juxtaposed material such as edges defining the at least one opening and/or aperture and, some embodiments, at least part of the marker band(s) and/or marker region(s) may also be at least partially echolucent relative to surrounding or juxtaposed material, including other marker band(s) and/or marker region(s) and relatively echogenic edges defining opening(s) and/or aperture(s).

Still more alternatively, the echogenicity, or echolucence may vary or differ along the length and/or around the circumference, of an echogenic, or echolucent, marker band or marker region by varying the echogenicity and/or echolucence of the material therealong or therearound to adjust the ultrasonic acoustic impedance of the marker band or marker region.

Still further, the relative echogenicity (or echolucence) of an edge defining an opening and/or aperture may vary or differ around its perimeter, wherein a portion or portions of the edge may be more or less echogenic (or echolucent) than remaining portions. In one embodiment, the edge may comprise a series of portions, that may be in a pattern, that comprise varying echogenicity, but wherein the edge will comprise a minimum echogenicity that is greater than the echolucent opening and/or aperture defined thereby.

Moreover, a relatively (compared with surrounding or juxtaposed materials) echogenic band, e.g., a solid metal band comprising echolucent openings or apertures defined by edges, may comprise a pattern along and/or around the cannula, the pattern being descriptive of a certain cannula feature to aid in locating the subject cannula feature within the image and related anatomy. A combination of such echolucent opening(s) or aperture(s), and relatively echogenic defining edges may therefore provide such an identification pattern. A similar patterned result may be provided using a coating and/or deposits of echolucent materials in discrete regions on a relatively echogenic band to form a pattern of echolucence. Alternatively, a patterned result may be provided using a coating and/or deposits of echogenic materials in discrete regions comprising a pattern on a relatively echolucent band. As discussed above, the relative and/or patterned echogenicity vs echolucence provided therefore may also be provided in combination with the at least partially echogenic marker hands and/or regions described above to form an identification pattern for certain cannula features and location thereof. For example, the blood pump inlet region, the blood pump outlet region and/or the blood pump impeller region or other key regions of the intravascular medical device may be identified and located in this way.

A pattern of echolucent openings) or aperture(s), with relatively echogenic edges may comprising, for example, increasing or decreasing frequency along (either axially or diagonally or other pattern generally comprising a proximal and distal endpoint and/or starting point) and/or around the cannula. In addition, the sizes may increase or decrease along and/or around the cannula, including but not limited to size changes axially, diagonally or circumferentially or radially, or other pattern generally comprising a proximal and distal endpoint and/or starting point. Other functionally equivalent patterns are readily obtained and within the scope of the present invention. Similarly, a coating and/or depositing of echogenic material on an echolucent band may comprise a pattern as described herein. Still further, the coating and/or deposits may comprise echolucent material on an echogenic band to form a pattern.

Figure 3A:
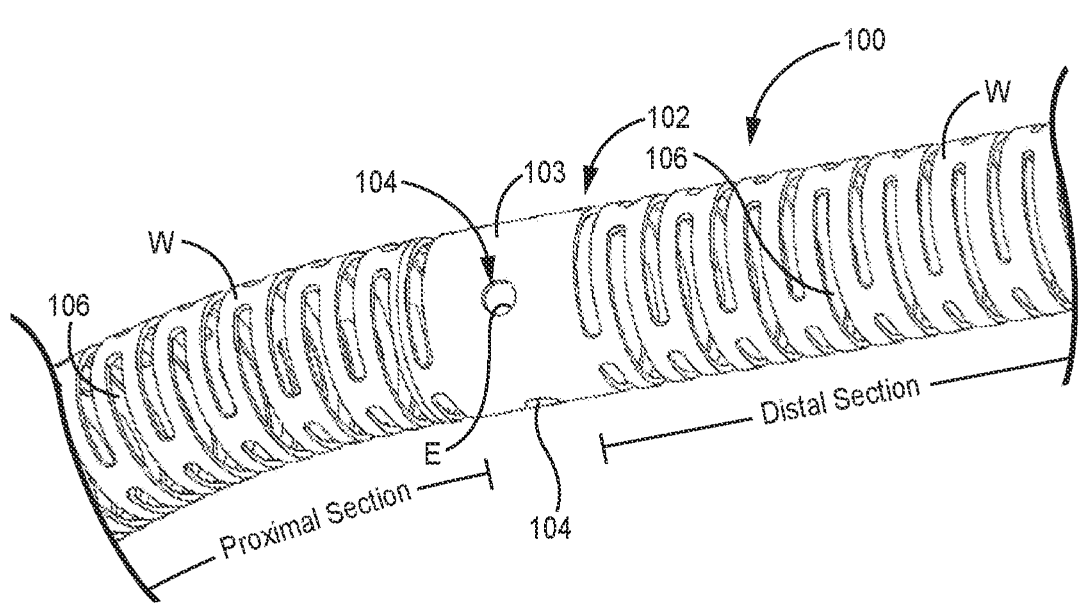
FIG. 3A is a side cutaway view of one embodiment of the present invention.

Turning now to FIG. 3A, an elongated cannula 1 comprising a wall W and defining a lumen extending from a proximal end of the cannula to a distal end of the medical cannula. An region of enhanced echogenicity 102 is provided and which comprises the wall W formed primarily of a solid echogenic material 103, e,g., a metal or partially metal, with enhanced contrast echolucent aperture(s) 104 defined therethrough. As shown in FIG. 3A, cannula 100 comprises an exemplary laser-cut tube comprising proximal and distal sections having flexibility slots 106, and an echogenic region 102 which is disposed between proximal and distal sections. The artisan will recognize that the flexibility slots 106 are also echolucent while the intervening wall W material is relatively echogenic. The echogenic region 102 comprises a relatively large and unbroken echogenic field, e.g., a solid metal band, broken only by the defined apertures 104 which are echolucent, thus providing the identifying and locating functionalities. This arrangement provides a bright imaging background with echolucent aperture(s) 104 disposed therein as described above. The artisan will also understand that the enhanced echogenic region 102 may be positioned at any point along the cannula 1, including at a distal or proximal end thereof.

Generally, the echogenic region 102, e.g., an echogenic solid metal band, may be incorporated into cannula wall W, attached to cannula wall W, formed from cannula wall W, and/or comprise a portion of cannula wall W in various embodiments. The skilled artisan will recognize the various ways to include the echogenic region, e.g., solid metal band, and further such methods or structures apply to all embodiments discussed herein.

Moreover, in all embodiments, the artisan will recognize the imaging utility of providing echolucent openings or apertures, e.g., 104, that comprise a different size and/or a different shape and/or a different orientation than any laser cut openings, e.g., 106 along the remaining portion of the exemplary laser-cut tube.

The echogenic region 102 defines the one or more echogenic aperture(s) or opening(s) 104 which are echolucent regions defined within the very echogenic unbroken field of the echogenic region 103 which comprises echogenic material 103. Each echolucent aperture 104 is defined by edges E formed by the echogenic material 103, wherein the at least one opening or aperture 104 is echolucent and therefore identifiable via non-invasive means (e.g. ultrasound, echocardiogram, x-ray, fluoroscopy) when the cannula 100 is positioned within a patient's body when viewed in combination with the relatively echogenic edges F defining the at least one opening and/or aperture which appears brighter in contrast compared with the opening or aperture. In this manner, a highly contrasting juxtaposition of echogenicity vs echolucence is provided for imaging purposes and is, therefore, more easily identifiable during the imaging process. As discussed further below, an echolucent region may be provided that may be entirely, or partially, echolucent. The echolucent region may in some embodiments comprise regions of echogenic material.

The at least one opening or aperture 104 may comprise least one circular opening or aperture and may be echolucent relative to the surrounding or juxtaposed echogenic material 103, including but not limited to relatively echogenic and defining edges E which is more echogenic, than echolucent opening or aperture 104. As illustrated, the at least one opening or aperture 101 is defined through a solid (non-stented or otherwise interrupted) band that forms a portion of the cannula. The artisan will understand that the shape of the at least one opening or aperture 104 need not be circular and may be formed of any geometric shaping to obtain similar functionality, therefore the opening may comprise, without limitation, a circle, an oval, a conical shape, a slot, a square, a rectangle, and/or a polygonal shape.

The at least one opening or aperture 104, and echogenic edges E defining same, may comprise an equal spacing (equally spaced apart) pattern between adjacent openings or apertures 104 and edge(s) E thereof around the circumference of the cannula, or may comprise a pattern of spacing that is non-equal, e.g., decreasing spacing between adjacent opening or aperture 104 and edge(s) E thereof in one circumferential direction, or increasing spacing in the opposite circumferential direction. In addition, the size of the at least one opening or aperture 104, and edge(s) E thereof, may be constant or may change, i.e., larger or smaller, in one circumferential direction around the cannula. The artisan will recognize that any pattern of the at least one opening or aperture 104 may be provided, or they may be randomly disposed on the echogenic region 102.

Applicable to all embodiments described herein, the exemplary solid metal band illustrating the echogenic region 102, and that defines the at least one opening or aperture 104 may be at least partially echogenic in order to provide an imaging reflective contrast with the echolucent at least one opening or aperture 104. FIG. 3A provides such a solid band that defines the at least one opening or aperture 104, each defined by a relatively echogenic edge E.

Also applicable to all embodiments described herein, a solid band defining the at least one opening or aperture 102 may comprise a gradient (a form of a pattern) of echogenicity (or echolucence) along the axial length of the solid band in a proximal or distal direction, and/or around the circumference of the solid hand. As discussed above, the edge E defining an opening or aperture 104 may also comprise an echogenicity exceeding the echogenicity of both the defined opening and aperture 104 as well as at least portions of the enhanced region of echogenicity 102. In some embodiments the echogenicity of the edge E may be the same, may be less, or may be greater than the echogenicity of the echogenic material 103 of the solid field defining the echogenic region 102.

Figure 3B:
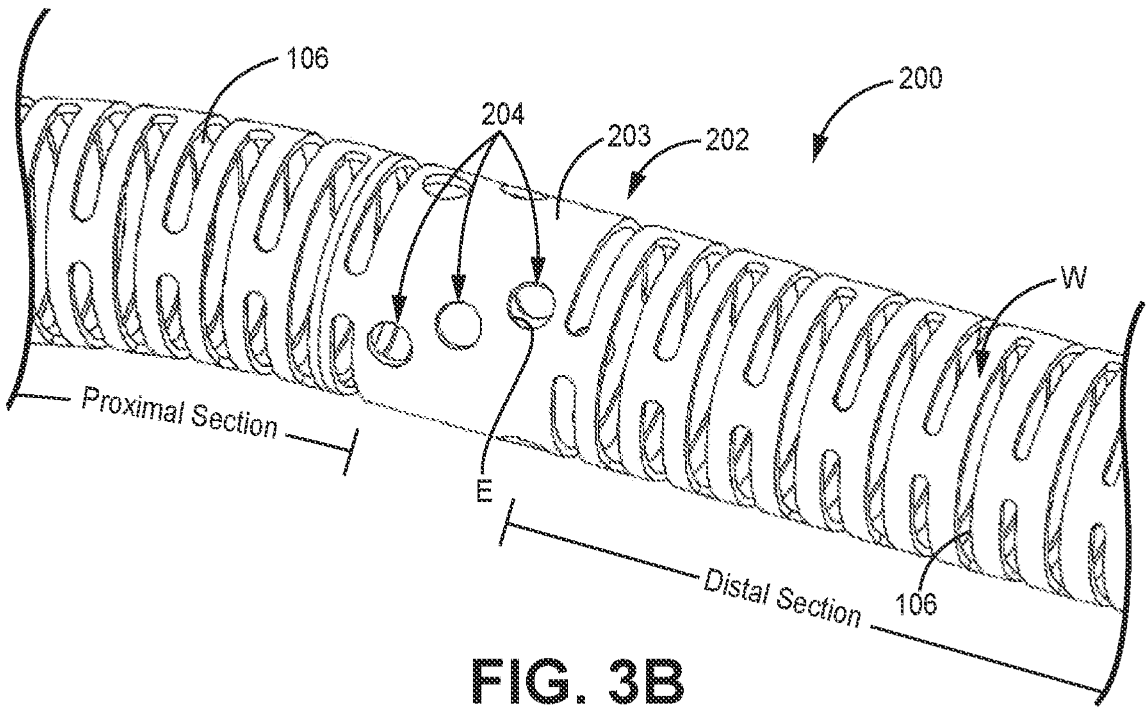
FIG. 3B is a side cutaway view of one embodiment of the present invention.

In another embodiment, as shown in FIG. 3B, exemplary laser cut cannula 200 may comprise at least one opening 204 as a plurality of exemplary circular openings or apertures 204 arranged in a plurality of repeating diagonal pattern groupings. As in FIG. 3A, the at least one opening or aperture 204 is defined by edges E formed through region of echogenicity 202 comprising an echogenic material such as a metal.

As shown, circumferentially adjacent diagonal pattern groupings of the exemplary openings or apertures 204 are spaced apart at a distance that is greater than a diagonal spacing between the openings or apertures 204 within each diagonal pattern group.

The diagonal pattern comprising a pattern group illustrated in FIG. 3B is merely exemplary as is the circular shaping of openings or apertures 204. Any patterning of openings or apertures 204, and corresponding relatively echogenic edges E defining openings 204, may be used. In certain embodiments, the spacing distance between the adjacent openings or patterns 204 within each pattern is smaller than the circumferential spacing distance between adjacent pattern groups. Further, the openings or apertures 204, and corresponding edges E of relatively greater echogenicity, shown below are all of substantially similar size and shape. However, the openings or apertures 204, and corresponding edges E, may vary in size and/or shape within each pattern group. Further, openings or apertures 204 and corresponding edges E may vary in size and/or shape across pattern groups such that, e.g., a first pattern group comprises a first size and/or shape of openings or apertures 204, and an adjacent second pattern group comprises a second size and/or shape of openings or apertures 204 that differs from the first size and/or shape of openings or apertures 204 in the first pattern group.

This general construction of pattern groups and sizing and shaping of the openings or apertures 204, and corresponding edges E defining openings or apertures 204, within the pattern groups applies to all embodiments discussed herein that comprise pattern groups of relatively echolucent openings or apertures and the relatively echogenic edges defining the openings or apertures. A similar construction of patterns may be provided by a coating and/or deposits of echogenic or echolucent material on a surface of the region of echogenicity exemplified by a solid metal band (or echolucence exemplified by a solid echolucent band) discussed herein.

Figure 3C:
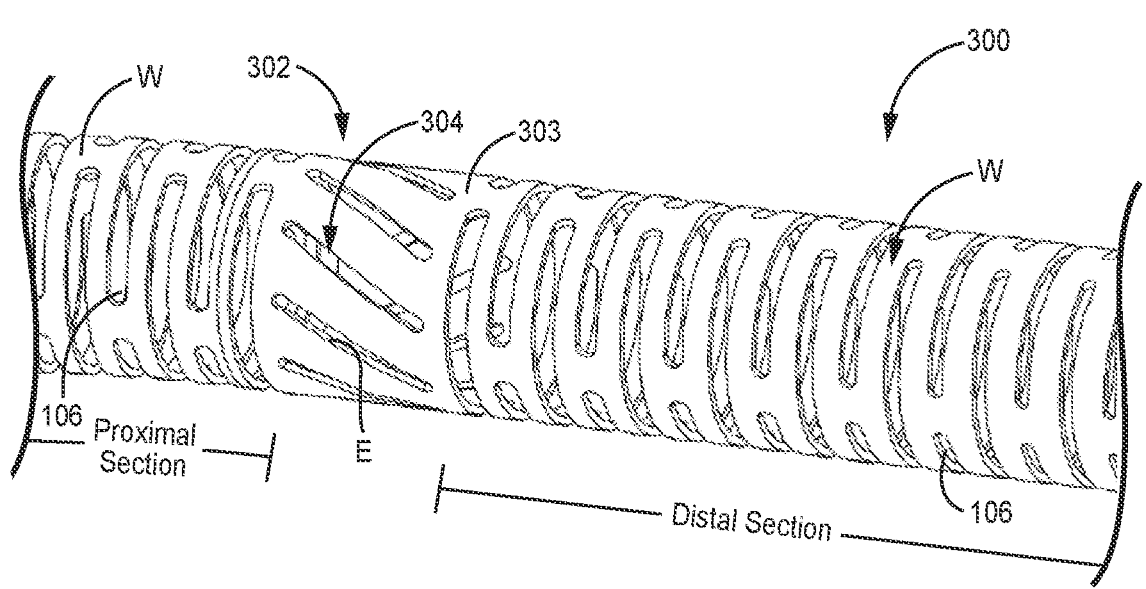
FIG. 3C is a side cutaway view of one embodiment of the present invention.

In another embodiment, as shown in FIG. 3C which is a variation of FIGS. 3A and 3B, provides exemplary laser cut cannula 300 comprising the at least one opening or aperture 304 as a slot shape; e.g., a plurality of slots 304 defined by relatively echogenic edges E and within echogenic region 402, e.g., a solid metal band, comprising relatively echogenic material 403. Slots 304, and corresponding edges E, may be arranged in pattern groups as described above and may vary in size and/or shape also as described above. For example, and without limitation, instead of a rectangular shaped or symmetrically shaped opening, a tear drop shape or a conical shape or other shape may be employed.

Figure 3D:
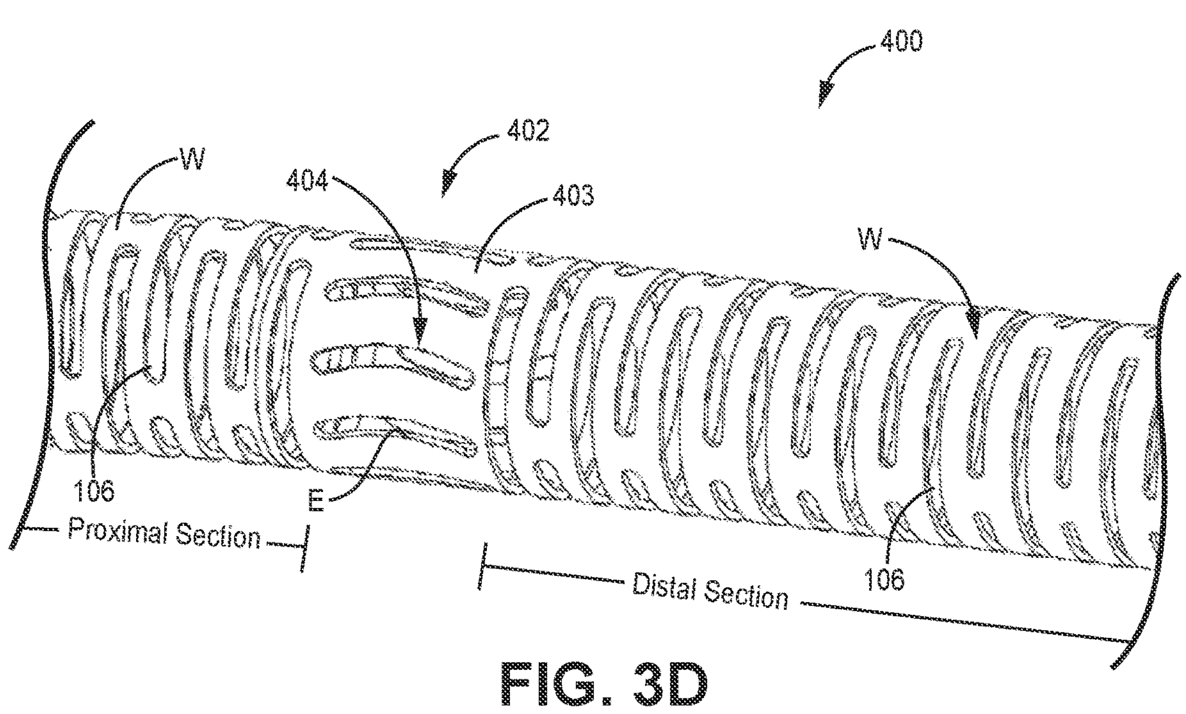
FIG. 3D is a side cutaway view of one embodiment of the present invention.

In another embodiment, as shown in FIG. 3D, exemplary laser cut cannula 400 comprises the at least one opening or aperture 404 as at least one curved slot; e.g., a plurality of curved slots 400 defined by relatively greater echogenic edges E through the region of enhanced echogenicity 402 comprising relatively echogenic material 403. Curved slots 404, and corresponding edges, may be arranged in pattern groups as described above and may vary in size and/or shape as described above.

Each of the embodiments of FIGS. 3A-3D, comprise echolucent openings or apertures are disposed within an echogenic region which is, in turn, disposed within or between proximal and distal sections of a laser-cut tube or cannula comprising, in turn, flexibility apertures 106. In all cases, the echolucent openings or apertures are of a different shape, size and orientation than the flexibility apertures 106, and further surrounded by a larger surface area field of echogenic material than the flexibility apertures 106. Each of these differential features taken individually, and/or in combination, enhance imaging of the region of enhanced echogenicity and of the openings or apertures defined therein.

Figure 4:
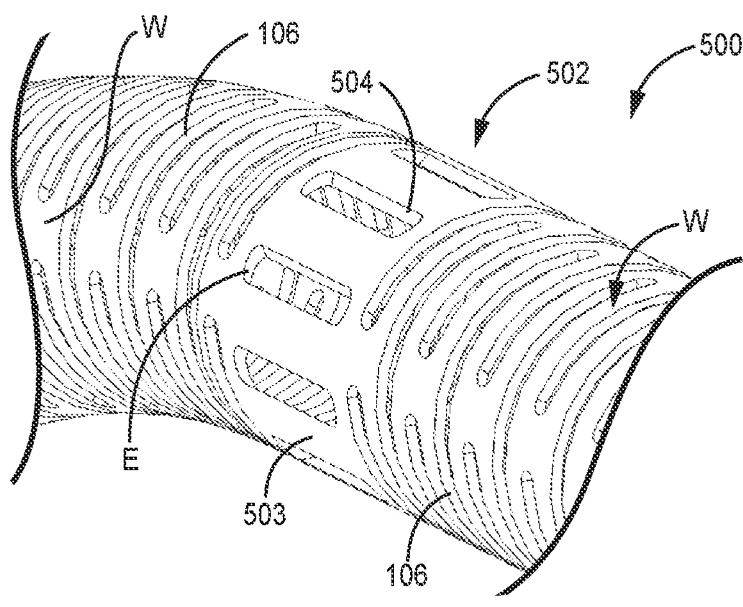
FIG. 4 is a perspective cutaway view of one embodiment of the present invention.

FIG. 4 illustrates an alternative arrangement of a cannula 400 having a plurality of exemplary openings or apertures 504 defined by relatively echogenic edges E compared with the echolucent openings or apertures 504 defined within the region of enhanced echogenicity 502 comprising relatively echogenic material 503. The openings or apertures 504 are disposed in an exemplary equal spacing circumferentially around the enhanced region of echogenicity 502. As before, any shaping or sizing of echolucent apertures 504 may be employed.

Figure 2:
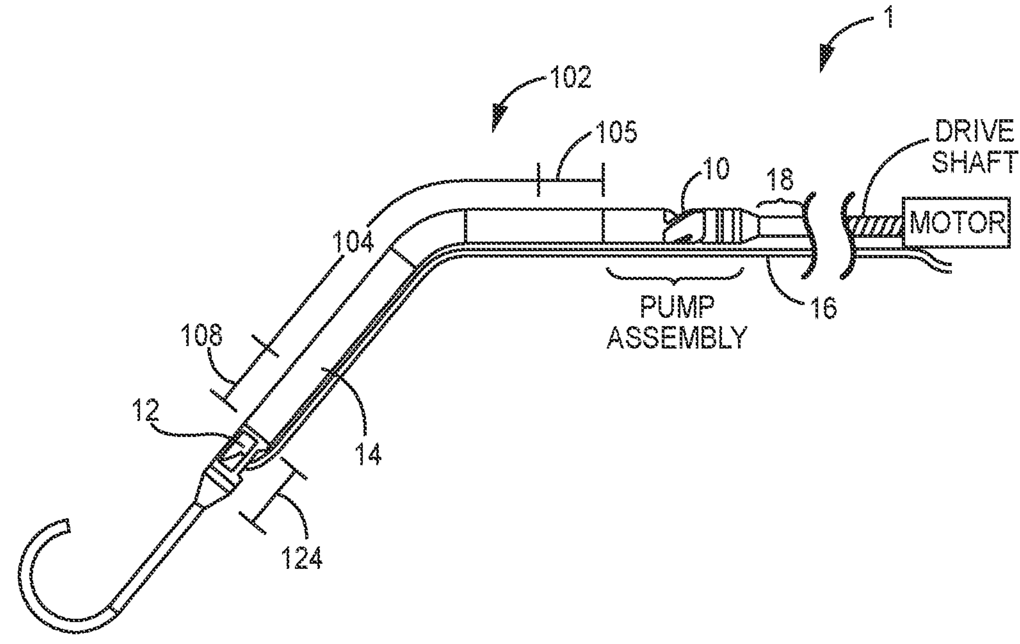
FIG. 2 is a side cutaway view of a prior art device.
Figure 5:
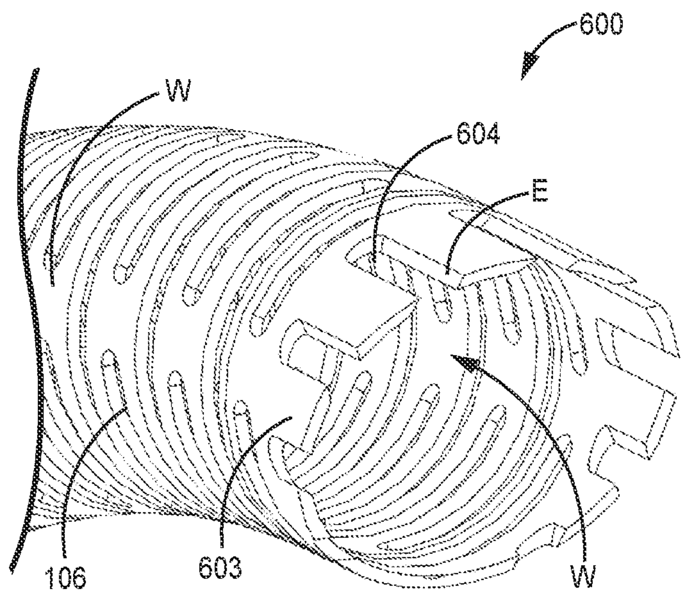
FIG. 5 is a perspective cutaway view of one embodiment of the present invention.

FIG. 5 provides another embodiment of an enhanced region of echogenicity 602 comprising echogenic material 603 and located or disposed at least one end (proximal and/or distal end) of tube or cannula 600. Exemplary flexibility slots 106 are provided in the exemplary laser cut tube and the echolucent openings or apertures are defined at an edge or end of the enhanced region of echogenicity 602 so that the openings or apertures are not completely enclosed at, or by edges E. In other embodiments the edges E may completely surround and define the openings or apertures 604. This configuration may be employed in an exemplary blood pump, wherein the enhanced region of echogenicity 602 is located at, or partially forms, inlet and/or outlet apertures as described in FIG. 2. Accordingly, a first and/or a second enhanced region of echogenicity 602, one or both of which may be located or form a distal end of the cannula or tube 600 may be provided. Alternatively, the enhanced region of echogenicity 602 may be provided just proximate to an angioplasty balloon or atherectomy working head, or other working device as described supra.

Figure 6:
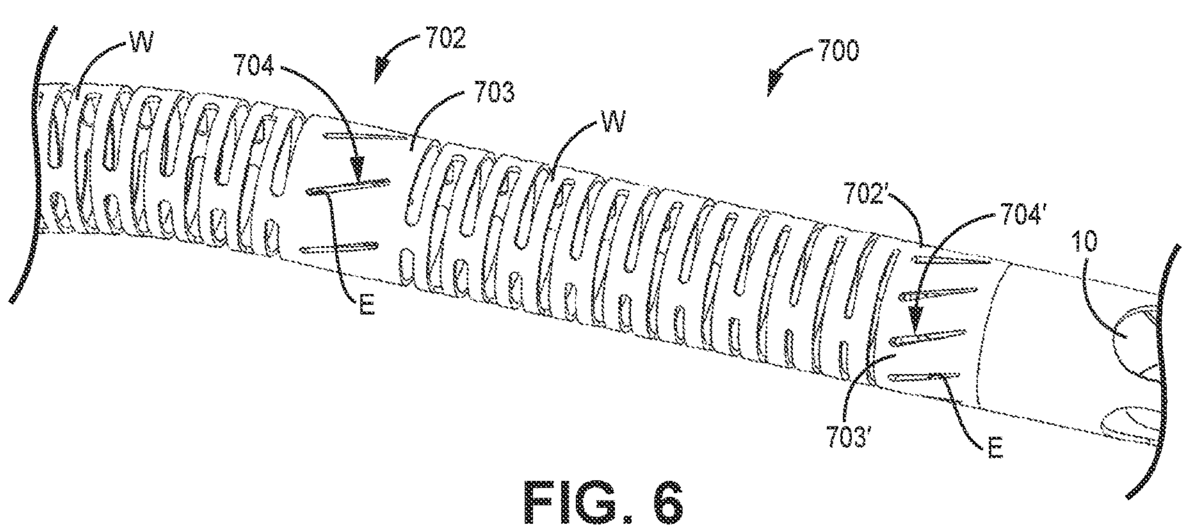
FIG. 6 is a perspective cutaway view of one embodiment of the present invention.

In another cannula or tube embodiment 700, as shown FIG. 6, two spaced-apart regions of enhanced echogenicity 702, 702' comprising at least one echogenic material 703, 703' are provided, wherein the at least one opening or aperture may comprise a plurality of diagonally arranged openings or apertures 704, 704', and corresponding edges E defining openings or apertures 704, 704', that may vary in pattern frequency and/or size and/or shape and wherein the edges E comprise a higher echogenicity compared with that of the openings or apertures 704, 704 and, in some cases, the relatively echogenic material 703, 703' of the enhanced regions of echogenicity 702, 702'. As shown, openings or apertures 704' are disposed proximate to exemplary outlet apertures 10 of an exemplary blood pump cannula such as described above. Alternatively, as described above, opening or aperture 704' may form or define at least part of the outlet apertures 10 of exemplary blood pump to enhance visual imaging of that region during locating and operation. As above, one or both of the openings or apertures 704, 704' may be positioned proximate to an atherectomy device's working head and/or an angioplasty balloon. The artisan will recognize that the apertures 704, 704' may, or may not, be of the same shape, size or orientation at each region of enhanced echogenicity 702, 702. Any combination of shape, size and/or orientation may be employed.

Figure 7:
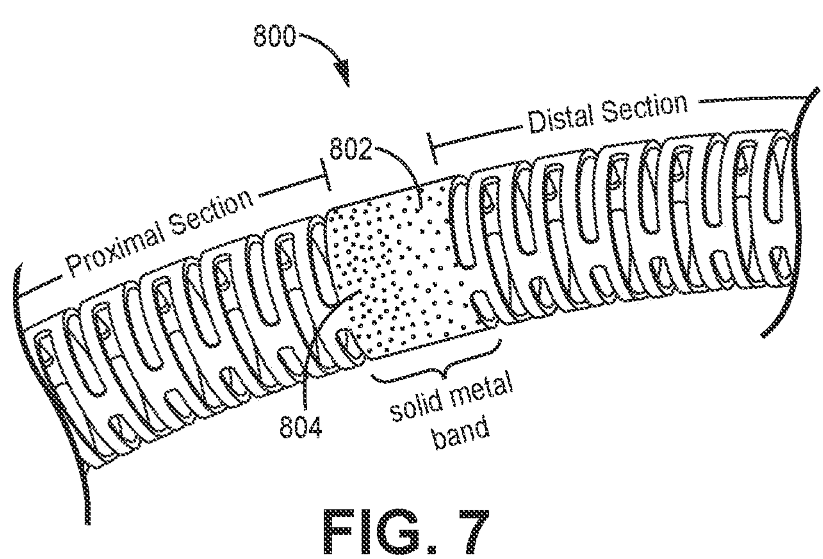
FIG. 7 is a perspective cutaway view of one embodiment of the present invention.

In the embodiment of FIG. 7, a cannula or tube 800 comprising an echogenic region 802 exemplified as a solid metal band comprising material that is at least partially echolucent material 804 (illustrated as dots on the solid metal band) is provided between proximal and distal cannula regions having different echogenicity characteristics to aid in identifying the solid marker band. The echolucent material may be coated on exemplary solid metal band in an increasing or decreasing thickness or concentration and/or may be deposited in discrete regions thereon and/or embedded therein. In a preferred embodiment, the exemplary solid metal band is echogenic, but may as described above comprise a gradient of echolucence (or echogenicity) axially (as illustrated using increasing density of dots to demonstrate an exemplary gradient) along the solid marker band and/or radially around the solid marker band. In the illustrated case, echogenicity is highest (echolucence lowest) at the proximal side of the region of enhanced echogenicity 802, with transition to decreasing echogenicity (and correspondingly increasing echolucence) moving in the distal direction across the solid marker band of the region of enhanced echogenicity 802. The artisan will recognize that the echogenic/echolucent gradient may be embodied in a variety of ways and patterns, including maximum echogenicity/minimum echolucence on or both of the proximal and/or distal edges of the solid marker band, or at any point therebetween.

An alternative embodiment comprises deposits or a coating of echolucent material on at least a portion of a surface of the echogenic edge(s) E to reduce edge E echogenicity relative to the echogenicity of the exemplary solid marker band, as in any of the embodiments illustrated in FIGS. 3A-6. In some embodiments, the reduced echogenicity of the exemplary solid marker band and edges E are substantially equivalent, with both structures receiving discrete deposits and/or coating of echolucent material.

Figure 8:
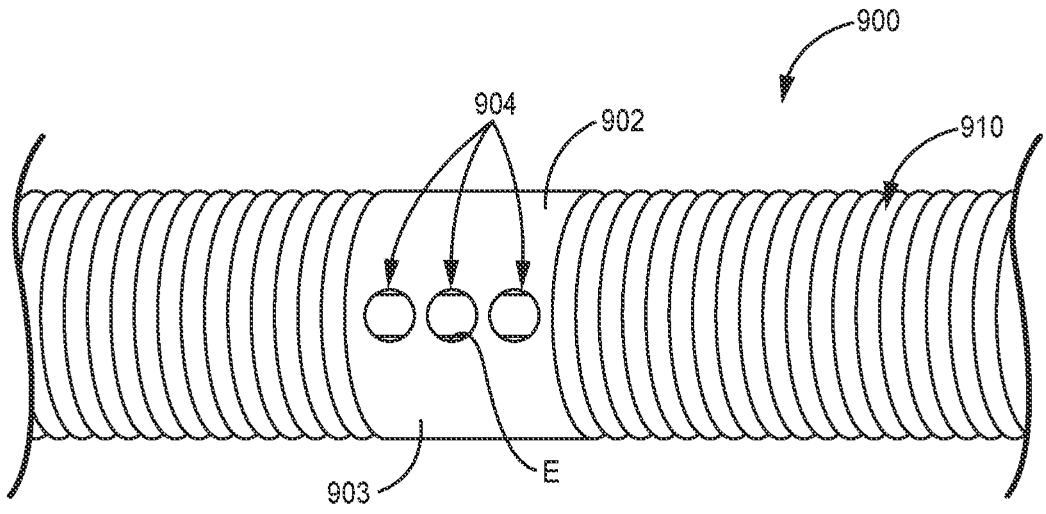
FIG. 8 is a side cutaway view of one embodiment of the present invention.

FIG. 8 illustrates an alternative tube 900 which may be a cannula or a catheter or a rotational drive shaft comprising one or more coiled wires with an echogenic region 902 comprising echogenic material 903 and defining one or more echolucent apertures 904 therein and comprising edges E having highly contrasting echogenicity compared with the echolucent opening(s) or aperture(s) 904. Tube 900 may be a rotational drive shaft or other device configured for introduction and use within a patient's vasculature, wherein the echogenic region 902 rotates with the coiled wires. As described above, one or more regions of echogenicity 902 may be provided. If more than one region of echogenicity is provided, they will be preferably axially spaced apart. Further, as above, at least one region of enhanced echogenicity may be provided at a distal and/or a proximal end of the tube 900.

As described above, the various embodiments comprising openings defined by a solid marker band or region are provided to modify the ultrasonic energy or waves that are reflected and observed in an imaging apparatus.

As also discussed above, materials may be used to alter the reflectance of ultrasonic energy or waves, i.e., to modify the acoustic impedance characteristics of the solid metal marker band and/or region.

The artisan will now readily understand that alternative arrangements of the structures of FIGS. 3A-8 may comprise at least one region of echolucence, interrupted by discrete regions or bands of echogenic material and/or adjacent to an echogenic region. In some embodiments, two spaced-apart echolucent regions or bands may be provided.

Thus, it is contemplated that regions of a medical cannula may comprise echolucent materials, alone or in combination with echogenic materials, in order to achieve the objectives of the present invention. Accordingly, e.g., in or along the cannula's length, a region may differentially (compared with adjacent regions) comprise a less echogenic (or more echolucent) material or coating.

Exemplary echolucent materials that may be used as described herein comprise, without limitation, polymeric materials such as nylon, polystyrene, vinyl, acrylic, polyvinyl chloride, and/or polycarbonate. In addition, such echolucent materials may be used to create regions of differing echogenicity and/or echolucence. For example, one marker band or region, and/or a cannula stent or laser-cut region, may comprise nylon while another spaced apart marker band or region may comprise polyvinyl chloride or other polymeric material with a different echolucence or acoustic impedance. Similarly, as described above, the polymeric materials may vary (as will be resulting acoustic impedance and echolucence) circumferentially around the cannula and/or marker band or region. Alternatively, discrete regions or deposits of echolucent material described herein may be deposited on, or coated on, an exemplary echogenic region such as a metal band and may comprise a pattern moving circumferentially and/or axially—for example the density of echolucent deposits or coating may increase (or decrease) moving across the echogenic region or metal band in a proximal to distal direction (or distal to proximal direction).

Echogenic materials may also be embedded or otherwise disposed within an otherwise at least partially echolucent marker, band or region. For example, discrete deposits of echogenic metallic material such as tungsten, or stainless steel or nitinol (nickel and titanium alloy) may be embedded within an echolucent material to provide additional visual identity of the subject cannula region. As described above, the metallic deposits may comprise a pattern wherein they are uniformly spaced apart, may comprise a longitudinal and/or circumferential pattern or may be randomly spaced apart. Such metallic deposits may comprise a thin band, metal flakes, drops, beads or fibers.

Alternatively, an echolucent, or partially echolucent solid band comprising echolucent material(s) may be provided on a cannula or tube as described herein. In certain embodiments, a region of enhanced echogenicity as described supra may be disposed adjacent with, or spaced apart from, the echolucent or partially echolucent solid band to provide maximum imaging contrast. FIGS. 9A-10B illustrate alternate embodiments of these structures.

Figure 9A:
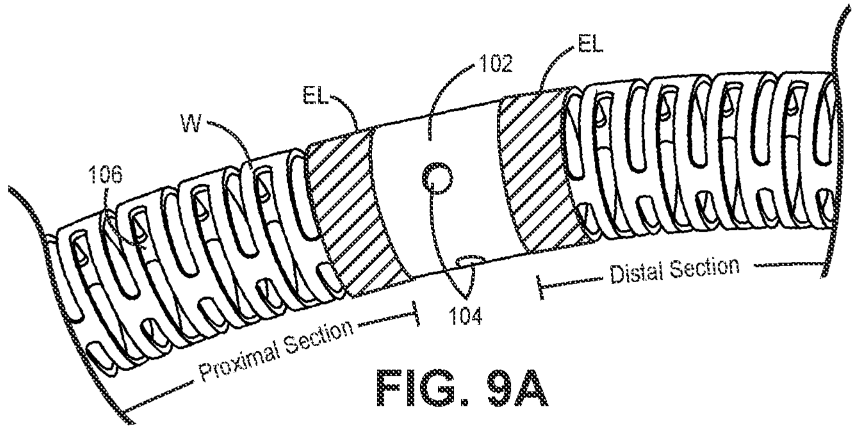
FIG. 9A is a side cutaway view of one embodiment of the present invention.
Figure 9B:
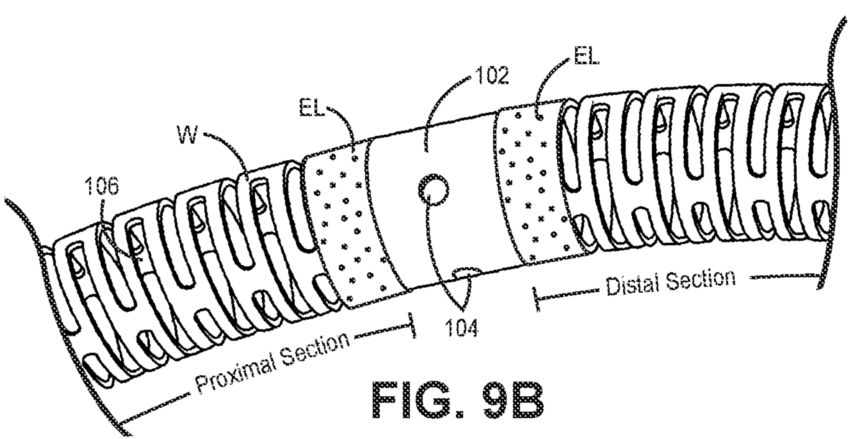
FIG. 9B is a side cutaway view of one embodiment of the present invention.
Figure 10A:
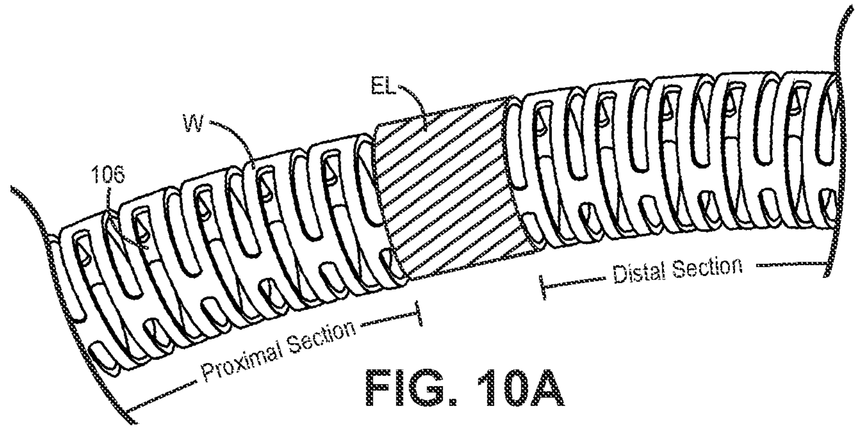
FIG. 10A is a side cutaway view of one embodiment of the present invention.
Figure 10B:
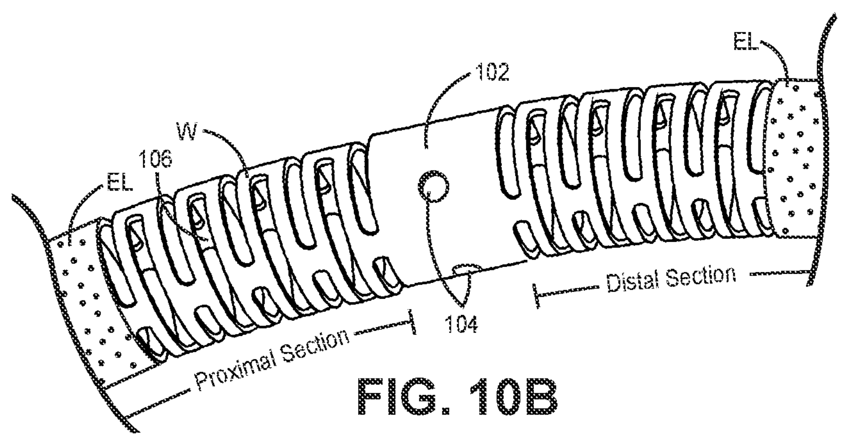
FIG. 10B is a side cutaway view of one embodiment of the present invention.

For example, as in FIGS. 9A, 9B and 10B, two or more spaced-apart echolucent, or partially echolucent, bands EL comprising echolucent material(s) may be provided. In some embodiments, an echogenic band, e.g., element 102 according to one of the embodiments described herein may be disposed between and/or adjacent and/or spaced apart from one or more of the spaced-apart echolucent or partially echolucent bands EL.

FIG. 9A illustrates an embodiment of a cannula wherein two echolucent bands EL are disposed on or incorporated into the cannula wall, with a first echolucent band EL disposed adjacent the proximal side of an echogenic solid metal ring 102 and a second echolucent band EL disposed on the distal side of the echogenic solid metal ring 102. Echogenic solid metal ring 102 may, as shown, or may not, comprise echolucent features such as openings or apertures 104 and/or discrete regions of echolucent deposits and/or coatings.

FIG. 9B is a variation of the embodiment of FIG. 9A wherein the cannula comprises an echogenic solid metal ring 102 without echolucent material or features thereon, and with the first and second echolucent bands EL disposed adjacent to the proximal and distal sides, respectively, of the echogenic solid metal ring 102. One, or both, of the echolucent bands EL may, as shown, comprise discrete deposits and/or coatings of echogenic material (illustrated as discrete dots in FIG. 9B) which may be patterned or may be randomly positioned.

FIG. 10A illustrates an exemplary cannula embodiment wherein one or more echolucent bands EL may be located along, or attached to, or incorporated with, the cannula, without a related echogenic band, e.g., element 102 in FIG. 9A. FIG. 10A shows two spaced-apart echolucent bands EL disposed at opposing ends, e.g., proximal and distal ends, of the cannula.

In the Figures, each of the one or more echolucent openings or apertures are defined by more echogenic edges E and disposed within the echogenic field of a solid band comprising echogenic material. In some embodiments, the echogenicity of the edges E may be the same as, less than, or greater than the echogenicity of the echogenic field of the solid band comprising echogenic material.

The various embodiments described herein may comprise a cannula or tube or drive shaft or catheter having an outer wall that comprises one or more of: a laser-cut tube, a polymer, a braid, a stent, and/or one or more coiled wires.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A medical cannula comprising:

an outer wall defining a lumen extending from a proximal end of the cannula to a distal end of the medical cannula, the outer wall comprising at least one region of enhanced echogenicity;

at least one echolucent region attached to, or comprising a portion of, the at least one region of enhanced echogenicity, wherein the at least one echolucent region comprises one or more discrete regions of deposits, or coating, of echolucent material thereon, wherein the discrete regions of deposits, or coating, of echogenic material form at least one circumferential and/or axial pattern of echolucence.

2. The medical cannula of claim 1, wherein the at least one echolucent region comprises at least two spaced-apart echolucent regions, wherein one of the at least two echolucent regions is disposed at a proximal end of the medical cannula.

3. The medical cannula of claim 2, wherein at least one of the at least two spaced-apart echolucent regions is disposed at a distal end of the medical cannula.

* * * * *